United States Patent [19]
Buzna et al.

[11] 3,949,077
[45] Apr. 6, 1976

[54] SYNERGISTIC ANTIBIOTIC COMPOSITIONS

[75] Inventors: Árpád Buzna; Gábor Kulcsar; Jenö Soltesz, All of Debrecen, Hungary; Tibor Vályi Nagy, deceased, late of Debreoen, Hungary, by Flora Valyi Nagy, legal representative

[73] Assignee: Chinoin Gyogyszer-es Vegyeszeti Termekek Gyara RT, Budapest, Hungary

[22] Filed: Sept. 30, 1970

[21] Appl. No.: 76,985

[30] Foreign Application Priority Data
Sept. 30, 1969 Hungary .............................. BU 503

[52] U.S. Cl. ............................................. 424/114
[51] Int. Cl. ........................................ A61k 21/00
[58] Field of Search ................................... 424/114

[56] References Cited
FOREIGN PATENTS OR APPLICATIONS
1,159,568   7/1969   United Kingdom ................. 424/115

OTHER PUBLICATIONS
New and Nonofficial Drugs 1964, J. B. Lippincott Co., Phila., Pa., pp. 60–62.
The Merck Index, 8th Edition, 1968, Merck & Co., Inc. Rahway, N.J., pp. 776–777.
Chemical Abstracts 74:30745s (1971).

Primary Examiner—Jerome D. Goldberg
Attorney, Agent, or Firm—Hubbell, Cohen & Stiefel

[57] ABSTRACT

The antibiotic primycin synergizes the effect of other antibiotics when used together therewith in amounts such that the primycin constitutes 5 to 50% by weight of the total antibiotic content.

12 Claims, No Drawings

SYNERGISTIC ANTIBIOTIC COMPOSITIONS

This invention is directed to antibiotic compositions possessing synergistic activity and a process for the preparation thereof. More particularly, it is concerned with antibiotic compositions containing primycin.

It is known that certain pathogenic microorganisms show different behavior against various antibiotics. It is also known that certain strains may become resistant to some antibiotics.

Research in the field of antibiotics led, on the one hand to the development of so called wide-spectrum antibiotics exhibiting higher activity than previously known strains, and on the other hand, to the inhibition of the development of resistance. The spectrum of activity may also be extended by the combined application of more than one antibiotic optionally mixed together with chemotherapeutical agents.

The so called synergistic effect is known in connection with chemotherapeutical agents, and also with respect to other biologically active compounds. This results in the fact that when more than one drug is simultaneously applied, the presence of the second component results in a significant increase in the activity of the drug. The opposite effect (so called antagonistic effect) is also known.

The mutual effect of simultaneously applied antibiotics exerted on each other and on various pathogenic microorganisms has been studied for a long time. These experiments showed unambiguously that among the previously known antibiotics, both synergism and antagonism may occur. In the case of synergism the therapeutic activity of the combination increases significantly in the treatment of various infections (so called mixed infections). This is probably due to the fact that the components of the antibiotic combination attack the metabolism of the microorganism simultaneously at several sites. Thus the microorganism has a smaller chance of developing resistance against the antimicrobial agent. Moreover, due to the simultaneous effect of several metabolic routes, a bactericidic rather than a bacteriostatic effect takes place.

Synergism between antibiotics may appear not only as a quantitative increase in the activity, but also as a qualitative change in the activity. This means that certain antibiotic combinations may inhibit the growth of microorganisms against which the components alone are completely or almost completely ineffective.

It has been generally found that the occurance of synergism is not influenced substantially either by the absolute concentration of the components or by the ratio of the concentrations.

A further advantage of antibiotic combinations is that in the course of prolonged administration the toxicity of the individual components is reduced to a significant extent and this may result in a considerable reduction of the administered effective doses of the components. This point of view may be of significant importance particularly when certain expensive compositions are concerned.

According to a feature of the present invention, there are provided antibiotic combinations comprising primycin or derivatives thereof in admixture with at least one known antibiotic and optionally with suitable inert pharmaceutically acceptable carriers and/or excipients.

The present invention is based on the recognition that the antibiotic primycin is particularly suited to increase the activity of known antibiotics and in certain cases even to an extension of the spectrum of activity.

Primycin is an antibiotic produced by culturing a Micromonospora galerienses strain as described in British Pat. No. 1.159,568. Primycin may be used also in the form of derivatives thereof.

The other component or components of the antibiotic compositions according to the present invention may be any known antibiotics showing synergism when administered simultaneously with primycin. A large number of known antibiotics are suitable for this purpose. As antibiotics exhibiting synergistic effects with primycin, there may be mentioned the tetracyclines, such as tetracycline, oxytetracycline, chlorotetracycline, demethyltetracycline, or neomycin, peptide-type antibiotics, e.g., viomycin, streptomycin, semi-synthetic penicillins, such as oxacillin, methicillin, ampicillin, etc. and derivatives thereof.

The ratio of the concentration of the active ingredients may vary over wide ranges. It is preferred to use 5–50% by weight of primycin calculated on the total antibiotic content of the composition. At concentration below 5% by weight the synergistic effect is rather low, while above 50% the synergistic effect is not increased generally by the augmentation of the primycin content.

The compositions may optionally further contain therapeutically active components, particularly chemotherapeutic agents, e.g., sulfonamides, dichlorohydroxychinaldine, etc.

The antibiotic combinations according to the present invention may optionally contain suitable inert pharmaceutically acceptable carriers and/or excipients. Said carriers may be those generally used in the pharmaceutical arts, such as starch, talc, magnesium carbonate, magnesium stearate, calcium carbonate, etc. The compositions according to the present invention may also contain other additives, such as filling, disintegrating, and lubricating agents, etc.

The compositions according to the present invention may be finished in solid (e.g., tablets, pills, coated pills, suppositories, capsules), semisolid (e.g., ointments) or liquid form (e.g., injectable preparation, solutions, suspensions or emulsions). The compositions may be administered orally, parenterally or rectally.

The antibiotic compositions according to the present invention may also be used in veterinary therapy. The compositions are particularly suitable for the treatment of mastitis. The compositions may be applied orally or topically. When administered orally, the compositions may be in the form of powder mixtures, suspensions or ointments. The powder mixtures may contain in addition to the active ingredients suitable inert carriers, such as sugar, starch, etc. One may also proceed by incorporating the powder mixture consisting of the active ingredients into the animal fodder. Suspensions may be particularly used for the treatment of sucking animals. The suspensions may preferably be prepared by suspending the active ingredients in honey. The ointments may be prepared by uniformly incorporating the active ingredients into conventional ointment bases such as petroleum jelly, etc.

When administered topically the compositions according to the present invention may be preferably in the form of ointments, aqueous or oily emulsions, aqueous or oily suspensions, vulnerary powders, aerosols, sprays or capsules.

A particularly preferred composition according to the present invention comprises equal amounts of primycin, neomycin or a salt thereof and oxytetracycline or a salt thereof.

The dosage of the antibiotic compositions according to the present invention may vary over very wide ranges and always depends on the requirements of the given situation, the nature of the infection, the condition of the patient, etc. In veterinary therapy daily doses between about 4 mg and about 30 mg per kg. body of weight may be administered, but considerably lower or higher doses may be used as well.

According to a further feature of the present invention, there is provided a process for the preparation of antibiotic compositions having synergistic effect, which comprises admixing primycin or a derivative thereof with at least one known antibiotic capable of exhibiting a synergistic effect, when administered together with primycin and optionally with suitable inert pharmaceutically acceptable carriers and/or excipients.

The derivatives of primycin and the antibiotics, which may be used in the process according to the present invention are those disclosed above.

The preparation of the compositions according to the present invention may be carried out by methods known in the pharmaceutical arts. Thus the primycin or a derivative thereof may be admixed with the further antibiotic and with suitable inert carriers and/or other additives and/or excipients. The carriers, additives and excipients may be those enumerated above.

The antibiotic compositions according to the present invention exert synergistic activity against a number of pathogenic microorganisms, such as Bacillus subtilis, E.coli, sensitive and polyresistant Staphylococcus strains, Mycobacterium tuberculosis, Candida albicans, etc.

The biological activity (in vitro) of the antibiotic compositions according to the present invention is shown by the following tests.

TEST 1

Combination of neomycin and primycin.

As may be seen from Table 1 a potentiating synergism is observed.

Against Bacillus Subtilis neomycin is active in a dose of 2.5 $\gamma$/ml and primycin in a dose of 0.5 $\gamma$/ml. When the combination is applied, the minimal effective dose is 0.25 $\gamma$/ml + 0.25 $\gamma$/ml.

Against Staphylococcus 209 P neomycin and primycin show inhibition in a concentration of 0.5 $\gamma$/ml and 0.25 $\gamma$/ml respectively. When the combination is administered, inhibition is achieved in a concentration of 0.05 $\gamma$/ml + 0.05 $\gamma$/ml.

Against the fungal strain Candida albicans neomycin primycin are active in a concentration of 100 $\gamma$/ml and 20 $\gamma$/ml respectively. The active concentration of the combination amounts to 10 $\gamma$/ml + 10 $\gamma$/ml respectively.

TEST 2

Combination of oxytetracycline and primycin.

As shown in table 2, against Bacillus subtilis, the minimal active concentration of the two individual components amounts to 0.5 $\gamma$/ml each. When the combination is administered the effect is achieved by using concentrations of 0.125 $\gamma$/ml + 0.125 $\gamma$/ml.

The growth of E.coli is inhibited by oxytetracycline in a concentration of 100 $\gamma$/ml. Primycin proved to be ineffective. The minimal inhibiting concentration of the combination amounts to 50 $\gamma$/ml + 50 $\gamma$/ml.

Against Staphylococcus 209 P, oxytetracycline and primycin exhibit inhibiting effect in a concentration of 0.5 $\gamma$/ml and 0.25 $\gamma$/ml respectively. The inhibiting concentration of the combination amounts to 0.125 $\gamma$/ml + 0.125 $\gamma$/ml.

It is seen from Table 2 that in connection with the combination of primycin and oxytetracycline potentiating synergism takes place.

TEST 3

Combination of viomycin and primycin.

It may be seen from Table 3 that against Staphylococcus 209 P, viomycin and primycin are active in a concentration of 5 $\gamma$/ml and 0.25 $\gamma$/ml respectively. The effective concentration of the combination amounts to 0.125 $\gamma$/ml + 0.125 $\gamma$/ml.

Against Candida albicans viomycin proved to be ineffective and the minimal effective concentration of primycin amounts to 20 $\gamma$/ml. The combination proved to be effective in a concentration of 10 $\gamma$/ml + 10 $\gamma$/ml.

It is clear that the combination of primycin and viomycin exhibits a potentiating synergistic effect.

TEST 4

Combination of streptomycin and primycin.

As shown in Table 4, streptomycin and primycin are active against Bacillus subtilis in a minimal concentration of 0.25 $\gamma$/ml and 0.5 $\gamma$/ml respectively. The effective concentration of the combination amounts to 0.125 $\gamma$/ml + 0.125 $\gamma$/ml.

Against E.coli $o_{111}$ streptomycin is active in a concentration of 100 $\gamma$/ml, while primycin does not inhibit said microorganism. The combination is ineffective in a dose of 25 $\gamma$/ml + 25 $\gamma$/ml.

Against Candida albicans, streptomycin and primycin are active in a concentration of 100 $\gamma$/ml and 20 $\gamma$/ml respectively. The effective concentration of the combination amounts to 12.5 $\gamma$/ml + 12.5 $\gamma$/ml.

It is evident on the basis of the above results that the combination of streptomycin and primycin exhibits a potentiating synergistic effect.

TEST 5

Combination of oxacillin and primycin.

It may be seen from Table 5 that this combination also exerts a potentiating synergistic activity. Against Bacillus subtilis oxacillin and primycin are active in a concentration of 1.0 $\gamma$/ml and 0.5 $\gamma$ml, respectively. When administered simultaneously, the effective concentration amounts to 0.25 $\gamma$/ml + 0.25 $\gamma$/ml.

TEST 6

Combination of neomycin, oxytetracycline and primycin.

It may be seen from Table 6 that a potentiating synergistic effect may also be observed when the combination comprises three components.

Against Bacillus subtilis, neomycin, oxytetracyclin and primycin are active in a concentration of 2.5 $\gamma$/ml, 0.5 $\gamma$/ml and 0.5 $\gamma$/ml respectively. The effective concentration of the combination amounts to 0.166 $\gamma$/ml + 0.166 $\gamma$/ml + 0.166 $\gamma$/ml.

Against E.coli $o_{111}$ neomycin and oxytetracycline are active in a dose of 25 $\gamma$/ml and 100 $\gamma$/ml respectively. Primycin proved to be ineffective. The effective concentration of the combination amounts to 16.6 $\gamma$/ml +

16.6 γ/ml + 16.6 γ/ml.

Against Staphylococcus 209 P neomycin, oxytetracycline and primycin are active in a concentration of 0.5 γ/ml, 0.5 γ/ml and 0.25 γ/ml respectively. The effective concentration of the combination amounts to 0.083 γ/ml and 0.083 γ/ml.

Against Candida albicans, neomycin, oxytetracycline and primycin are active in a concentration of 100 γ/ml, 100 γ/ml and 20 γ/ml respectively. The inhibiting concentration of the combination was found to be 8.3 γ/ml + 8.3 γ/ml + 8.3 γ/ml.

TEST 7

Combination of candicidin and primycin.

As shown in Table 7, against Procandida albicans, a polyresistant fungal strain, candicidin and primycin are active in a concentration of 0.05 γ/ml and 50 γ/ml respectively. The effective concentration of the combination amounts to 0.01 γ/ml + 25 γ/ml. A potentiating synergistic effect is observed in this case also.

TEST 8–10

The synergistic effect of combinations of primycin, neomycin and oxytetracycline; primycin and oxytetracyclin; and primycin and neomycin respectively is shown in Tables 8–13. It may be seen that the effective concentration of the combinations are significantly lower than those of individual components.

The following definitions are used in the tables:
φ no growth of bacteria
± very weak but still detectable
+ weak growth of bacteria
++ medium growth of bacteria
+++ strong growth of bacteria The last lines in Tables 8–13 show the minimal effective concentration of the antibiotics.

Tables 1–6 relate to tests carried out on pathogens of humans, while Tables 7–13 are concerned with tests effected by using pathogens of animals.

| | | Table 1 | | | Table 2 | |
|---|---|---|---|---|---|---|
| | | Neomycin + Primycin | | | Oxytetracycline+ Primycin | |
| Concentration (γ)/ml | | B. subtilis | Staph. 209 P | Candida albicans | B. subtilis | E. Coli 111 | Staphy- lococcus 209 P |
| 50 + 50 | | φ | φ | φ | φ | φ | φ |
| 25 + 25 | | φ | φ | φ | φ | +++ | φ |
| 12.5 + 12.5 | | φ | φ | φ | φ | +++ | φ |
| 10 + 10 | | φ | φ | φ | φ | +++ | φ |
| 5 + 5 | | φ | φ | +++ | φ | +++ | φ |
| 2.5 + 2.5 | | φ | φ | +++ | φ | +++ | φ |
| 1.25 + 1.125 | | φ | φ | +++ | φ | +++ | φ |
| 0.5 + 0.5 | | φ | φ | +++ | φ | +++ | φ |
| 0.25 + 0.25 | | φ | φ | +++ | φ | +++ | φ |
| 0.125 + 0.125 | | ++ | φ | +++ | φ | +++ | φ |
| 0.05 + 0.05 | | +++ | φ | +++ | +++ | +++ | ++ |
| Control | | +++ | +++ | +++ | +++ | +++ | +++ |
| Minimal active concentration | Other antibioticum | 2.5γ | 0.5γ | 100γ | 0.5γ | 100γ | 0.5γ |
| | Primycin | 0.5γ | 0.25γ | 20γ | 0.5γ | <100γ | 0.25γ |

| | | Table 3 | | Table 4 | | Table 5 | |
|---|---|---|---|---|---|---|---|
| | | Viomycin + Primycin | | Streptomycin + Primycin | | Oxacillin+ Primycin | |
| Concentration (γ)/ml | | Staph. 209 P | Candida albicans | B. subtilis | E. coli 111 | Candida albicans | B. subtilis |
| 50 + 50 | | φ | φ | φ | φ | φ | φ |
| 25 + 25 | | φ | φ | φ | φ | φ | φ |
| 12.5 + 12.5 | | φ | φ | φ | +++ | φ | φ |
| 10 + 10 | | φ | φ | φ | +++ | +++ | φ |
| 5 + 5 | | φ | +++ | φ | +++ | +++ | φ |
| 2.5 + 2.5 | | φ | +++ | φ | +++ | +++ | φ |
| 1.25 + 1.25 | | φ | +++ | φ | +++ | +++ | φ |
| 0.5 + 0.5 | | φ | +++ | φ | +++ | +++ | φ |
| 0.25 + 0.25 | | φ | +++ | φ | +++ | +++ | φ |
| 0.125 + 0.125 | | φ | +++ | φ | +++ | +++ | +++ |
| 0.05 + 0.05 | | +++ | +++ | ++ | +++ | +++ | +++ |
| Control | | +++ | +++ | ++ | +++ | +++ | +++ |
| Minimal active concentration | other antibiotic | 5γ | <100γ | 0.25γ | 100γ | 100γ | 1γ |
| | Primycin | 0.25γ | 20γ | 0.5γ | <100γ | 20γ | 0.5γ |

Table 6

| Concentration (γ)/ml Primycin + Neomycin + Oxytetracycline | B. subtilis | E. coli 111 | Staph. 209 P | Candida albicans |
|---|---|---|---|---|
| 33.3 + 33.3 + 33.3 | φ | φ | φ | φ |
| 16.6 + 16.6 + 16.6 | φ | φ | φ | φ |
| 8.3 + 8.3 + 8.3 | φ | ++ | φ | φ |
| 6.6 + 6.6 + 6.6 | φ | +++ | φ | +++ |
| 3.3 + 3.3 + 3.3 | φ | +++ | φ | +++ |
| 1.66 + 1.66 + 1.66 | φ | +++ | φ | +++ |
| 0.83 + 0.83 + 0.83 | φ | +++ | φ | +++ |
| 0.33 + 0.33 + 0.33 | φ | +++ | φ | +++ |
| 0.166 + 0.166 + 0.166 | φ | +++ | φ | +++ |
| 0.083 + 0.083 + 0.083 | +++ | +++ | φ | +++ |

Table 6-continued

| Concentration (γ)/ml Primycin + Neomycin + Oxytetracycline | B. subtilis | E. coli 111 | Staph. 209 P | Candida albicans |
|---|---|---|---|---|
| 0.033 + 0.033 + 0.033 | +++ | +++ | +++ | +++ |
| Control | +++ | +++ | +++ | +++ |
| Minimal active concentration — Neomycin | 2.5γ | 25γ | 0.5γ | 100γ |
| Minimal active concentration — OTC | 0.5γ | 100γ | 0.5γ | 100γ |
| Minimal active concentration — Primycin | 0.5γ | <100γ | 0.25γ | 20γ |

OTC = Oxytetracycline

Table 7

| Concentration (γ/ml) Candicidin + Primycin | Incubation period | Concentration (γ/ml) Candicidin + Primycin | Incubation period | Concentration (γ/ml) Candicidin + Primycin | Incubation period |
|---|---|---|---|---|---|
| 0.03 + 50 | 48ʰ φ | 0.02 + 50 | 48ʰ φ | 0.01 + 50 | 48ʰ φ |
| 0.03 + 25 | φ | 0.02 + 25 | φ | 0.01 + 25 | φ |
| 0.03 + 10 | φ | 0.02 + 10 | ++ | 0.01 + 10 | +++ |
| 0.03 + 5 | φ | 0.02 + 5 | ++ | 0.01 + 5 | +++ |
| Control | +++ | Control | +++ | Control | +++ |
| Minimal active concentration Candicidin γ/ml | 0.05 | | 0.05 | 0.05 | 0.05 | 0.05 |
| Minimal active concentration Primycin γ/ml | 50 | | 50 | 50 | 50 | 50 |

Table 8

| γ/ml | Streptococcus aequi (atypical) | | Streptococcus ubaris 2. | | Streptococcus ubaris 4. | | Streptococcus agalactiae 1 | | Streptococcus agalactiae 6 | | Streptococcus dysgalactiae | | Bacterium flora originated from excrement | | Bacterium flora originated from the vagina | |
|---|---|---|---|---|---|---|---|---|---|---|---|---|---|---|---|---|
| Period | 24ʰ | 48ʰ | 24ʰ | 48ʰ | 24ʰ | 48ʰ | 24ʰ | 48ʰ | 24ʰ | 48ʰ | 24ʰ | 48ʰ | 24ʰ | 48ʰ | 24ʰ | 45ʰ |
| 100 | φ | φ | φ | φ | φ | φ | φ | φ | φ | φ | φ | φ | ++ | +++ | + | +++ |
| 50 | φ | φ | φ | φ | φ | φ | φ | φ | φ | φ | φ | φ | +++ | +++ | +++ | +++ |
| 25 | φ | φ | φ | φ | φ | φ | φ | φ | φ | φ | φ | φ | +++ | +++ | +++ | +++ |
| 10 | φ | φ | φ | φ | φ | φ | φ | φ | φ | φ | φ | φ | +++ | +++ | +++ | +++ |
| 5 | φ | φ | φ | φ | φ | φ | φ | φ | φ | φ | φ | φ | +++ | +++ | +++ | +++ |
| 4 | φ | φ | φ | φ | φ | φ | φ | φ | φ | φ | φ | φ | +++ | +++ | +++ | +++ |
| 3 | φ | φ | φ | φ | φ | φ | φ | φ | φ | φ | φ | φ | +++ | +++ | +++ | +++ |
| 2 | φ | φ | φ | φ | φ | φ | φ | φ | φ | φ | φ | φ | +++ | +++ | +++ | +++ |
| 1 | φ | φ | φ | +++ | φ | +++ | +++ | +++ | φ | φ | φ | φ | +++ | +++ | +++ | +++ |
| 0.75 | φ | φ | φ | +++ | +++ | +++ | +++ | +++ | φ | φ | φ | φ | +++ | +++ | +++ | +++ |
| 0.5 | φ | ++ | +++ | +++ | +++ | +++ | +++ | +++ | φ | φ | φ | φ | +++ | +++ | +++ | +++ |
| 0.25 | +++ | +++ | +++ | +++ | +++ | +++ | +++ | +++ | φ | φ | ± | + | +++ | +++ | +++ | +++ |
| 0.1 | +++ | +++ | +++ | +++ | +++ | +++ | +++ | +++ | +++ | +++ | +++ | +++ | +++ | +++ | +++ | +++ |

Table 9

Neomycin sulfate

| γ/ml | Streptococcus aequi (atypical) | | Streptococcus ubaris 2. | | Streptococcus ubaris 4. | | Streptococcus agalactiae 1. | | Streptococcus agalactiae 6 | | Streptococcus dysgalactiae | | Bacterium flora originated from excrement | | Bacterium flora originated from the vagina | |
|---|---|---|---|---|---|---|---|---|---|---|---|---|---|---|---|---|
| | 24ʰ | 48ʰ | 24ʰ | 48ʰ | 24ʰ | 48ʰ | 24ʰ | 48ʰ | 24ʰ | 48ʰ | 24ʰ | 48ʰ | 24ʰ | 48ʰ | 24ʰ | 48ʰ |
| 100 | φ | φ | φ | φ | φ | φ | φ | +++ | φ | φ | φ | φ | +++ | +++ | φ | φ |
| 75 | φ | φ | φ | +++ | φ | φ | φ | +++ | φ | φ | φ | φ | +++ | ++ + | φ | φ |
| 50 | φ | φ | φ | +++ | φ | ++ | + | +++ | φ | φ | φ | φ | +++ | +++ | φ | φ |
| 25 | φ | φ | ++ | +++ | ± | +++ | +++ | +++ | φ | φ | φ | φ | +++ | +++ | φ | φ |
| 10 | φ | φ | +++ | +++ | +++ | +++ | +++ | +++ | φ | φ | φ | φ | +++ | +++ | φ | +++ |
| 7.5 | φ | +++ | +++ | +++ | +++ | +++ | +++ | +++ | φ | φ | φ | φ | +++ | +++ | +++ | ++ + |
| 5 | +++ | +++ | +++ | +++ | +++ | +++ | +++ | +++ | φ | φ | φ | φ | +++ | +++ | +++ | +++ |
| 2.5 | +++ | +++ | +++ | +++ | +++ | +++ | +++ | +++ | φ | φ | φ | φ | +++ | +++ | +++ | +++ |
| 1 | +++ | +++ | +++ | +++ | +++ | +++ | +++ | +++ | φ | φ | φ | φ | +++ | +++ | +++ | +++ |
| 0.75 | +++ | +++ | +++ | +++ | +++ | ++ + | +++ | +++ | φ | φ | φ | φ | +++ | +++ | +++ | +++ |
| 0.5 | +++ | +++ | +++ | +++ | +++ | +++ | +++ | +++ | ± | +++ | +++ | +++ | +++ | +++ | +++ | +++ |
| 0.25 | +++ | +++ | +++ | +++ | +++ | +++ | +++ | +++ | +++ | +++ | +++ | +++ | +++ | +++ | +++ | +++ |
| 0.1 | +++ | +++ | +++ | +++ | +++ | +++ | +++ | +++ | + | +++ | +++ | + ++ | +++ | +++ | +++ | +++ |
| Control | +++ | +++ | +++ | +++ | +++ | +++ | +++ | ++ | +++ | +++ | +++ | +++ | +++ | +++ | +++ | +++ |

Table 10

Oxytetracycline HCl

| μg/ml | Streptococcus aequi (atypical) | | Streptococcus uberis 2 | | Streptococcus uberis 4 | | Streptococcus agalactiae 1 | | Streptococcus agalactiae 6 | | Streptococcus dysgalactiae | | Bacterium flora originated from excrement | | Bacterium flora originated from the vagina | |
|---|---|---|---|---|---|---|---|---|---|---|---|---|---|---|---|---|
| | $24^h$ | $48^h$ | $24^h$ | $48^h$ | $24^h$ | $48^h$ | $24^h$ | $48^h$ | $24^h$ | $48^h$ | $24^h$ | $48^h$ | $24^h$ | $48^h$ | $24^h$ | $48^h$ |
| 100 | φ | φ | φ | φ | φ | φ | φ | φ | φ | φ | φ | φ | +++ | +++ | +++ | +++ |
| 50 | φ | φ | φ | φ | φ | φ | φ | φ | φ | φ | φ | φ | +++ | +++ | +++ | +++ |
| 25 | φ | φ | φ | φ | φ | φ | φ | φ | φ | φ | φ | φ | +++ | +++ | +++ | +++ |
| 10 | φ | φ | φ | φ | φ | φ | φ | φ | φ | φ | φ | φ | +++ | +++ | +++ | +++ |
| 5 | φ | φ | φ | φ | φ | φ | φ | φ | φ | φ | φ | φ | +++ | +++ | +++ | +++ |
| 4 | φ | φ | φ | φ | φ | φ | φ | φ | φ | φ | φ | φ | +++ | +++ | +++ | +++ |
| 3 | φ | φ | φ | φ | φ | φ | φ | φ | φ | φ | φ | φ | +++ | +++ | +++ | +++ |
| 2 | φ | φ | φ | ++ | φ | + | + | +++ | φ | φ | φ | φ | +++ | +++ | +++ | +++ |
| 1 | φ | φ | φ | +++ | ± | +++ | ++ | +++ | φ | φ | φ | + | +++ | +++ | +++ | +++ |
| 0.75 | φ | φ | +++ | +++ | ++ | +++ | +++ | +++ | φ | φ | φ | ++ | +++ | +++ | +++ | +++ |
| 0.5 | φ | ++ | +++ | +++ | +++ | +++ | +++ | +++ | φ | φ | ± | ++ | +++ | +++ | +++ | +++ |
| 0.25 | ++ | +++ | +++ | +++ | +++ | +++ | +++ | +++ | φ | ++ | ++ | +++ | +++ | +++ | +++ | +++ |
| 0.1 | +++ | +++ | +++ | +++ | +++ | +++ | +++ | +++ | ± | +++ | +++ | +++ | +++ | +++ | +++ | +++ |
| Control | +++ | +++ | +++ | +++ | +++ | +++ | +++ | +++ | +++ | +++ | +++ | +++ | +++ | +++ | +++ | +++ |

TABLE 11

PRIMYCIN + NEOMYCIN SULFATE

| Streptococcus aequi (atypical) | | | | Streptococcus uberis 2 | | | | Streptococcus uberis 4 | | | | Streptococcus agalactiae 1 | | | |
|---|---|---|---|---|---|---|---|---|---|---|---|---|---|---|---|
| Pr γ/ml | Neo γ/ml | $24^h$ | $48^h$ | Pr γ/ml | Neo γ/ml | $24^h$ | $48^h$ | Pr γ/ml | Neo γ/ml | $24^h$ | $48^h$ | Pr γ/ml | Neo γ/ml | $24^h$ | $48^h$ |
| 0.75 | +10 | φ | φ | 2 | +100 | φ | φ | 2 | +50 | φ | φ | 2 | +100 | φ | φ |
| 0.5 | +7.5 | φ | φ | 1 | +100 | φ | φ | 1 | +25 | φ | + | 1 | +100 | φ | φ |
| 0.5 | +0.5 | φ | ++ | 1 | +50 | φ | φ | 1 | +20 | φ | +++ | 0.5 | +100 | φ | φ |
| 0.25 | +0.25 | +++ | +++ | 0.5 | +100 | φ | φ | 1 | +10 | φ | +++ | 0.5 | +50 | φ | +++ |
| | | | | 0.5 | +50 | φ | ++ | 0.5 | +25 | φ | +++ | | | | |
| | | | | 1 | +25 | φ | +++ | 0.5 | +20 | φ | +++ | | | | |
| | | | | 0.5 | +25 | φ | +++ | 0.5 | +10 | ± | +++ | | | | |
| Control | | +++ | +++ | | | +++ | +++ | | | +++ | +++ | | | +++ | +++ |
| Neomycin 10 γ/ml | | φ | φ | 100 γ/ml | | φ | φ | 75 γ/ml | | φ | φ | | | | |
| Primycin 0.75 γ/ml | | φ | φ | 2 γ/ml | | φ | φ | 2 γ/ml | | φ | φ | 2 γ/ml | | φ | φ |

| Streptococcus agalactiae 6 | | | | Streptococcus dysgalactiae | | | | Bacterium flora originated from excrement | | | | Bacterium flora originated from the vagina | | | |
|---|---|---|---|---|---|---|---|---|---|---|---|---|---|---|---|
| Pr γ/ml | Neo γ/ml | $24^h$ | $48^h$ | Pr γ/ml | Neo γ/ml | $24^h$ | $48^h$ | Pr γ/ml | Neo γ/ml | $24^h$ | $48^h$ | Pr γ/ml | Neo γ/ml | $24^{25h}$ | $48^h$ |
| 0.25 | +0.75 | φ | φ | 0.5 | +0.75 | φ | φ | 100 | +100 | φ | ++ | 100 | +25 | φ | φ |
| 0.1 | +0.5 | ++ | +++ | 0.25 | +0.5 | φ | φ | 50 | +50 | ++ | +++ | 100 | +10 | φ | φ |
| 0.1 | +0.25 | +++ | +++ | 0.25 | +0.25 | φ | φ | 25 | +25 | ++ | +++ | 50 | +10 | φ | φ |
| 0.05 | +0.5 | +++ | +++ | 0.1 | +0.1 | +++ | +++ | 10 | +10 | +++ | +++ | 25 | +10 | φ | φ |
| 0.05 | +0.25 | +++ | +++ | | | | | 5 | +5 | +++ | +++ | 50 | +5 | φ | φ |
| | | | | | | | | | | | | 25 | +5 | φ | φ |
| | | | | | | | | | | | | 10 | +10 | φ | φ |
| | | +++ | +++ | | | +++ | +++ | | | +++ | +++ | | | +++ | +++ |
| 0.75 γ/ml | | φ | φ | 0.75 γ/ml | | φ | φ | | | | | 25 γ/ml | | φ | φ |
| 0.25 γ/ml | | φ | φ | 0.5 γ/ml | | φ | φ | | | | | | | | |

Pr = Primycin
Neo = Neomycin Sulfate
h = hours

TABLE 12

PRIMYCIN + OXYTETRACYCLINE HCl

| Streptococcus aequi (atypical) | | | | Streptococcus uberis 2 | | | | Streptococcus uberis 4 | | | | Streptococcus agalactiae 1 | | | |
|---|---|---|---|---|---|---|---|---|---|---|---|---|---|---|---|
| Pr γ/ml | OTC γ/ml | $24^h$ | $48^h$ | Pr γ/ml | OTC γ/ml | $24^h$ | $48^h$ | Pr γ/ml | OTC γ/ml | $24^h$ | $48^h$ | Pr γ/ml | OTC γ/ml | $24^h$ | $48^h$ |
| 0.76 | +1 | φ | φ | 2 | +3 | φ | φ | 2 | +3 | φ | φ | 2 | +4 | φ | φ |
| 0.75 | +0.75 | φ | φ | 1 | +2 | φ | φ | 1 | +2 | φ | φ | 1 | +3 | φ | φ |
| 0.5 | +0.5 | φ | φ | 1 | +1 | φ | ± | 1 | +1 | φ | φ | 1 | +2 | φ | φ |
| 0.25 | +0.25 | φ | ++ | 0.5 | +0.5 | ++ | +++ | 0.5 | +2 | φ | φ | 1 | +1 | ± | + |
| | | | | | | | | 0.5 | +1 | φ | φ | 0.5 | +2 | φ | φ |
| | | | | | | | | 0.5 | +0.5 | ± | ++ | 0.5 | +1 | ± | ++ |
| Pr γ/ml | OTC γ/ml | $24^h$ | $48^h$ | Pr γ/ml | OTC γ/ml | $24^h$ | $48^h$ | Pr γ/ml | OTC γ/ml | $24^h$ | $48^h$ | Pr γ/ml | OTC γ/ml | $24^h$ | $48^h$ |
| Control OTC | | +++ | +++ | | | +++ | +++ | | | +++ | +++ | | | +++ | +++ |
| 0.75 γ/ml Primycin | | φ | φ | 3 γ/ml | | φ | φ | 3 γ/ml | | φ | φ | 4 γ/ml | | φ | φ |

TABLE 12-continued

PRIMYCIN + OXYTETRACYCLINE HCl

| | Streptococcus aequi (atypical) | | | Streptococcus uberis 2 | | | Streptococcus uberis 4 | | | Streptococcus agalactiae 1 | | |
|---|---|---|---|---|---|---|---|---|---|---|---|---|
| 0.75 | γ/ml | φ | φ | 2 γ/ml | φ | φ | 2 γ/ml | φ | φ | 2 γ/ml | φ | φ |

| Streptococcus agalactiae 6 | | | | Streptococcus dysgalactiae | | | | Bacterium flora originated from excrement | | | | Bacterium flora originated from the vagina | | | |
|---|---|---|---|---|---|---|---|---|---|---|---|---|---|---|---|
| Pr γ/ml | OTC γ/ml | 24h | 48h | Pr γ/ml | OTC γ/ml | 24h | 48h | Pr γ/ml | OTC γ/ml | 24h | 48h | Pr γ/ml | OTC γ/ml | 24h | 48h |
| 0.25 | +0.5 | φ | φ | 0.5 | +2.5 | φ | φ | 100 | +100 | φ | φ | 100 | +100 | φ | φ |
| 0.1 | +0.25 | ± | + | 0.25 | +1 | φ | φ | 50 | +50 | +++ | +++ | 50 | +50 | +++ | +++ |
| 0.1 | +0.1 | + | ++ | 0.25 | +0.5 | φ | + | 25 | +25 | +++ | +++ | 25 | +25 | +++ | +++ |
| 0.05 | +0.05 | ++ | +++ | 0.25 | +0.25 | ± | ++ | 10 | +10 | +++ | +++ | 10 | +10 | +++ | +++ |
| | | | | 0.1 | +0.1 | +++ | +++ | 5 | +5 | +++ | +++ | 5 | +5 | +++ | +++ |
| | | | | | | | | 1 | +1 | +++ | +++ | 1 | +1 | +++ | +++ |
| Pr γ/ml | OTC γ/ml | 24h | 48h | Pr γ/ml | OTC γ/ml | 24h | 48h | Pr γ/ml | OTC γ/ml | 24h | 48h | Pr γ/ml | OTC γ/ml | 24h | 48h |
| | | +++ | +++ | | | +++ | +++ | | | +++ | +++ | | | +++ | +++ |
| 0.5 γ/ml | | φ | φ | 2 γ/ml | | φ | φ | | | | | | | | |
| 0.25 γ/ml | | φ | φ | 0.5 γ/ml | | φ | φ | | | | | | | | |

Pr = Primycin
OTC = Oxytetracycline HCl
h = hours

TABLE 13

PRIMYCIN + NEOMYCIN SULFATE + OXYTETRACYCLINE HCl

| Streptococcus aequi (atypical) | | | Streptococcus uberis 2 | | | Streptococcus uberis 4 | | | Streptococcus agalactiae 1 | | |
|---|---|---|---|---|---|---|---|---|---|---|---|
| Pr Neo OTC γ/ml | 24h | 48h | Pr Neo OTC γ/ml | 24h | 48h | Pr Neo OTC γ/ml | 24h | 48h | Pr Neo OTC γ/ml | 24h | 48h |
| 0.76+ 10+ 1 | φ | φ | 2+ 100+ 3 | φ | φ | 2+ 50+ 3 | φ | φ | 2+ 100+ 4 | φ | φ |
| 0.5+ 7.5+ 0.5 | φ | φ | 1+ 100+ 2 | φ | φ | 1+ 25+ 2 | φ | φ | 1+ 100+ 3 | φ | φ |
| 0.5+ 5+ 0.5 | φ | φ | 1+ 100+ 1 | φ | φ | 1+ 25+ 1 | φ | φ | 1+ 100+ 2 | φ | φ |
| 0.25+ 5+ 0.25 | φ | φ | 0.5+ 50+ 0.5 | φ | φ | 0.5+ 20+ 0.5 | φ | φ | 1+ 50+ 1 | φ | φ |
| Pr Neo OTC γ/ml | 24h | 48h | Pr Neo OTC γ/ml | 24h | 48h | Pr Neo OTC γ/ml | 24h | 48h | Pr Neo OTC γ/ml | 24h | 48h |
| | | | | | | 0.5+ 10+ 0.5 | φ | φ | 0.5+ 50+ 1 | φ | φ |
| Control | +++ | +++ | | +++ | +++ | | +++ | +++ | | +++ | +++ |
| Pr 0.75 γ/ml | φ | φ | 2 γ/ml | φ | φ | 2 γ/ml | φ | φ | 2 γ/ml | φ | φ |
| Pr Neo OTC γ/ml Neo 10 γ/ml OTC 0.75 γ/ml | 24h φ φ | 48h φ φ | Pr Neo OTC γ/ml 100 γ/ml 3 γ/ml | 24h φ φ | 48h φ φ | Pr Neo OTC γ/ml 75 γ/ml 3 γ/ml | 24h φ φ | 48h φ φ | Pr Neo OTC γ/ml 4 γ/ml | 24h φ | 48h φ |

| Streptococcus agalactiae 6 | | | Streptococcus dysgalactiae | | | Bacterium flora originated from excrement | | | Bacterium flora originated from the vagina | | |
|---|---|---|---|---|---|---|---|---|---|---|---|
| Pr Neo OTC γ/ml | 24h | 48h | Pr Neo OTC γ/ml | 24h | 48h | Pr Neo OTC γ/ml | 24h | 48h | Pr Neo OTC γ/ml | 24h | 48h |
| 0.25+ 0.75+ 0.5 | φ | φ | 0.5+ 0.75+ 2.5 | φ | φ | 100+ 100+ 100 | φ | φ | 100+ 25+ 100 | φ | φ |
| 0.1+ 0.5+ 0.25 | φ | φ | 0.25+ 0.5+ 1 | φ | φ | 50+ 50+ 50 | φ | ++ | 100+ 10+ 100 | φ | φ |
| 0.1+ 0.25 0.1 | φ | φ | 0.25+ 0.25+ 0.5 | φ | φ | 25+ 25+ 25 | φ | ++ | 50+ 10+ 50 | φ | φ |

TABLE 13-continued

PRIMYCIN + NEOMYCIN SULFATE + OXYTETRACYCLINE HCl

| Streptococcus aequi (atypical) | | | Streptococcus uberis 2 | | | Streptococcus uberis 4 | | | Streptococcus agalactiae 1 | | |
|---|---|---|---|---|---|---|---|---|---|---|---|
| 0.05+ | | | 0.25+ | | | 10+ | | | 25+ | | |
| 0.25+ | φ | ++ | 0.25+ | φ | + | 10+ | + | +++ | 10+ | φ | φ |
| 0.1 | | | 0.25 | | | 10 | | | 25 | | |
| Pr | | | Pr | | | Pr | | | Pr | | |
| Neo | 24ʰ | 48ʰ | Neo | 24ʰ | 48ʰ | Neo | 24ʰ | 48ʰ | Neo | 24ʰ | 48ʰ |
| OTC | | | OTC | | | OTC | | | OTC | | |
| γ/ml | | | γ/ml | | | γ/ml | | | γ/ml | | |
| 0.05+ | | | 0.1+ | | | 5+ | | | 10+ | | |
| 0.1+ | φ | ++ | 0.1+ | ± | ++ | 5+ | +++ | +++ | 10+ | φ | φ |
| 0.1 | | | 0.1 | | | 5 | | | 10 | | |
| | | | | | | 2.5+ | | | 5+ | | |
| | | | | | | 2.5+ | +++ | +++ | 5+ | | |
| | | | | | | 2.5 | | | 5 | φ | φ |
| | | | | | | 1+ | | | 1+ | | |
| | | | | | | 1+ | +++ | +++ | 1+ | +++ | +++ |
| | | | | | | 1 | | | 1 | | |
| | +++ | +++ | | +++ | +++ | | +++ | +++ | | | +++ |
| 0.25 γ/ml | φ | φ | 0.5 γ/ml | φ | φ | | | | | | |
| Pr | | | Pr | | | Pr | | | Pr | | |
| Neo | 24ʰ | 48ʰ | Neo | 24ʰ | 48ʰ | Neo | 24ʰ | 48ʰ | Neo | 24ʰ | 48ʰ |
| OTC | | | OTC | | | OTC | | | OTC | | |
| γ/ml | | | γ/ml | | | γ/ml | | | γ/ml | | |
| 0.75 | φ | φ | 0.75 | φ | φ | | | | 25 γ/ml | φ | φ |
| γ/ml | | | γ/ml | | | | | | | | |
| 0.5 | φ | φ | 2 γ/ml | φ | φ | | | | | | |
| γ/ml | | | | | | | | | | | |

Pr = Primycin
Neo = Neomycin Sulfate
OTC = Oxytetracycline HCl
h = hours

EXAMPLE 1

A powder mixture having the following composition is prepared by admixing the components enumerated below:

| Primycin | 10 g |
|---|---|
| Neomycin sulfate | 10 g |
| Oxytetracycline dihydrate | 10 g |
| Sugar | 70 g |

The powder mixture thus obtained is incorporated into animal fodder. The above dose is suitable for the treatment of 50 pigs, weighing 18–20 kg each.

EXAMPLE 2

The process described in Example 1 is carried out except that the components are used in the following amounts:

| Primycin | 3.34 g |
|---|---|
| Neomycin sulfate | 3.33 g |
| Oxytetracycline dihydrate | 3.33 g |
| Sugar | 90 g |

EXAMPLE 3

An ointment having the following composition is prepared:

| Primycin | 0.34 g |
|---|---|
| Neomycin sulfate | 0.33 g |
| Oxytetracycline dihydrate | 0.33 g |
| Petroleum jelly | 99 g |

EXAMPLE 4

A powder mixture consisting of
0.5 g of primycin
0.5 g of neomycin sulfate and
0.5 g of oxytetracyclinedihydrate is encapsulated by to known methods.

EXAMPLE 5

0.2 g of primycin
0.2 g of neomycin sulfate
0.2 g of oxytetracyclinedihydrate and
0.005 g of prednisolone
are dissolved in 10 ml of water and the solution is injected into the udder of cows.

EXAMPLE 6

Tablets having the following composition are prepared by admixing the ingredients in the amounts disclosed below:

| Primycin | 0.100 g |
|---|---|
| Oxytetracycline hydrochloride | 0.100 g |
| Neomycin sulfate | 0.100 g |
| Methylcellulose | 0.025 g |
| Luviskol VA 64 | 0.010 g |
| Lactose | 0.090 g |
| Potato starch | 0.055 g |
| Magnesium stearate | 0.006 g |
| Talc | 0.010 g |
| Aerosil 972 | 0.004 g |
| | 0.500 g |

Luviskol Va 64 is a vinyl polymer used as an emulsion stabilizer and Aerosil 972 is a silicilic acid having a surface area of 350 m²/gm and is also an emulsion stabilizer.

The tablets thus obtained may be used in human therapy. When administered to adult patients, the dose is 1–2 tablets a day for three days. Children may receive 1 tablet each day.

EXAMPLE 7

An ointment having the following composition is prepared:

| Primycin | 1.0 g |
| Oxytetracycline hydrochloride | 1.0 g |
| Neomycin sulfate | 1.0 g |
| Cera alba | 5.0 g |
| Solid Paraffin | 5.0 g |
| Liquid Paraffin | 39.0 g |
| Adeps lanae | 6.0 g |
| Petroluem Jelly | 42.0 g |
| | 100.0 g |

EXAMPLE 8

A dusting powder having the following composition is

| Primycin | 1.0 g |
| Oxytetracycline hydrochlorid | 1.0 g |
| Neomycin sulfate | 1.0 g |
| Magnesium carbonate | 10.0 g |
| Talcum | 87.0 g |
| | 100.0 g |

EXAMPLE 9

An aerosol spray is prepared by admixing 1% of primycin, 1% of oxytetraciclinehydrochloride and 1% of neomycin sulfate with a film forming agent (Plastubol). The mixture thus obtained is incorporated into an anhydrous carrier.

What we claim is:

1. A composition comprising equal amounts of primycin, neomycin sulfate and oxytetracycline in combination with a pharmaceutically acceptable carrier therefor.

* * * * *

UNITED STATES PATENT OFFICE

CERTIFICATE OF CORRECTION

Patent No. 3,949,077    Dated April 6, 1976

Inventor(s) ARPAD BUZNA et al    Page 1 of 3

It is certified that error appears in the above-identified patent and that said Letters Patent are hereby corrected as shown below:

Title page, left side, Inventors' address: "late of Debreoen," should read -- late of Debrecen, --.

Column 2, lines 24-25: "At concentration below 5% by weight" should read -- At concentrations below 5% by weight, --.

Column 3, lines 10-11: "30 mg per kg. body of" should read -- 30 mg per kg. of body --; line 15: "having synergistic" should read -- having a syngergistic --; line 61: "table 2" should read -- Table 2 --.

Column 4, line 60: "oxytetracyclin" should read -- oxytetracycline --.

Columns 7-8, Table 7, column 2, lines 4-5 under "Incubation period": "∅" should read -- + --.
∅           +

Columns 7-8, Table 8, last column, line 1 under "Bacterium flora originated from the vagina": "45h" should read -- $48^h$ --.

Columns 7-8, Table 9, column 5, line 2 under "Streptococcus ubaris 2 $48^h$": "+++" should read -- ++ --.

Columns 7-8, Table 9, column 8, line 10 under "Streptococcus agalactiae 1 $24^h$": "++ +" should read -- +++ --.

PO-1050
(5/69)

UNITED STATES PATENT OFFICE
CERTIFICATE OF CORRECTION

Patent No. 3,949,077      Dated April 6, 1976

Inventor(s) ARPAD BUZNA et al      Page 2 of 3

It is certified that error appears in the above-identified patent and that said Letters Patent are hereby corrected as shown below:

Columns 7-8, Table 9, column 13, line 2 from the bottom under "Streptococcus dysgalactiae": "+ ++" should read -- -- +++ --.

Columns 7-8, Table 9, column 15, line 2 under "Bacterium flora originated from excrement 48$^h$": "++ +" should read -- +++ --.

Columns 7-8, Table 9, last column, line 6 under "Bacterium flora originated from the vagina 48$^h$": "++ +" should read -- +++ --.

Columns 9-10, Table 10, first column, in the heading: "ug/ml" should read -- g/ml. --.

Columns 9-10, Table 12, first column, line 1 after "Pr ɣ/ml": "0.76" should read -- 0.75 --.

Columns 11-12, Table 13, first column, line 1 after " ɣ/ml": "0.76+" should read -- 0.75+ --.

Columns 11-12, Table 13, columns 7-8, lines 5-7 from the bottom under "Streptococcus uberis 4":
"Pr      " should read -- Pr      --.
   Neo   24$^h$           Neo     24$^h$
      OTC               OTC Columns 11-12, Table 13, columns 10-11, lines 3-5 from the bottom under "Streptococcus agalactia 1":

UNITED STATES PATENT OFFICE
CERTIFICATE OF CORRECTION

Patent No. 3,949,077     Dated  April 6, 1976

Inventor(s) ARPAD BUZNA et al     Page 3 of 3

It is certified that error appears in the above-identified patent and that said Letters Patent are hereby corrected as shown below:

"Pr
 Neo     24$^h$     "     should read  -- Pr
                                         Neo     24$^h$     --.
       OTC                                     OTC Columns 13-14, Table 13-continued, the headings:

" | Streptococcus aequi (atypical) | Streptococcus uberis 2 | Streptococcus uberis 4 | Streptococcus agalactiae 1 | "

should read:

-- | Streptococcus agalactiae 6 | Streptococcus dysgalactiae | Bacterium flora originated from excrement | Bacterium flora originated from the vagina | --.

Column 14, line 32: "oxytetracyclinedihydrate" should read -- oxytetracycline dihydrate --; line 33: "to known" should read -- known --; line 38: "oxytetracyclinedihydrate" should read -- oxytetracycline dihydrate --.

Column 15, line 14: "is" should read -- is prepared: --; line 17: "hydrochlorid" should read -- hydrochloride --.

Column 16, line 9: "oxytetraciclinehydrochloride" should read -- oxytetracycline hydrochloride --.

Signed and Sealed this

Twenty-ninth Day of March 1977

[SEAL]

Attest:

RUTH C. MASON
Attesting Officer

C. MARSHALL DANN
Commissioner of Patents and Trademarks